United States Patent
Flynn et al.

(10) Patent No.: US 7,763,873 B2
(45) Date of Patent: Jul. 27, 2010

(54) ION RADIATION THERAPY SYSTEM WITH VARIABLE BEAM RESOLUTION

(75) Inventors: Ryan Thomas Flynn, Iowa City, IA (US); Thomas R. Mackie, Verona, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 12/439,466

(22) PCT Filed: Feb. 27, 2008

(86) PCT No.: PCT/US2008/055096

§ 371 (c)(1),
(2), (4) Date: Feb. 27, 2009

(87) PCT Pub. No.: WO2008/106496

PCT Pub. Date: Sep. 4, 2008

(65) Prior Publication Data

US 2009/0189095 A1      Jul. 30, 2009

Related U.S. Application Data

(60) Provisional application No. 60/891,859, filed on Feb. 27, 2007.

(51) Int. Cl.
*A61N 5/00* (2006.01)
*G21K 1/00* (2006.01)

(52) U.S. Cl. .............. 250/505.1; 250/396 R; 250/492.3; 250/492.1; 315/500; 315/507; 315/111.81; 313/361.1; 313/359.1; 600/2

(58) Field of Classification Search .......... 250/505.1, 250/492.3, 396 R, 492.1; 315/500, 507, 315/111.81; 313/361.1, 359.1; 600/2
See application file for complete search history.

(56) References Cited

U.S. PATENT DOCUMENTS

| | | |
|---|---|---|
| 4,276,477 A | 6/1981 | Enge |
| 5,317,616 A | 5/1994 | Swerdloff et al. |
| 5,394,452 A | 2/1995 | Swerdloff et al. |
| 5,442,675 A | 8/1995 | Swerdloff et al. |
| 5,528,650 A | 6/1996 | Swerdloff et al. |
| 5,548,627 A | 8/1996 | Swerdloff et al. |
| 5,625,663 A | 4/1997 | Swerdloff et al. |
| 5,661,773 A | 8/1997 | Swerdloff et al. |

(Continued)

FOREIGN PATENT DOCUMENTS

DE         19907098 A1      8/2000

(Continued)

OTHER PUBLICATIONS

International Search Report, PCT Application No. PCT/US2008/055104, dated Jul. 17, 2008, ISA/EPO, 2280 HV Rijswijk, NL.

(Continued)

*Primary Examiner*—Nikita Wells
(74) *Attorney, Agent, or Firm*—Boyle Fredrickson, S.C.

(57) ABSTRACT

An ion radiation therapy machine provides a steerable beam for treating a tumor within the patient where the exposure spot of the beam is controlled in width and/or length to effect a flexible trade-off between treatment speed, accuracy, and uniformity.

8 Claims, 6 Drawing Sheets

U.S. PATENT DOCUMENTS

| | | | |
|---|---|---|---|
| 5,668,371 | A | 9/1997 | Deasy et al. |
| 5,673,300 | A | 9/1997 | Reckwerdt et al. |
| 5,724,400 | A | 3/1998 | Swerdloff et al. |
| 5,802,136 | A | 9/1998 | Carol |
| 6,345,114 | B1 | 2/2002 | Mackie et al. |
| 6,385,286 | B1 | 5/2002 | Fitchard et al. |
| 6,438,202 | B1 | 8/2002 | Olivera et al. |
| 6,560,311 | B1 | 5/2003 | Shepherd et al. |
| 6,618,467 | B1 | 9/2003 | Ruchala |
| 6,636,622 | B2 | 10/2003 | Mackie et al. |
| 6,661,870 | B2 | 12/2003 | Kapatoes et al. |
| 6,731,970 | B2 | 5/2004 | Scholssbauer et al. |
| 6,736,831 | B1 * | 5/2004 | Hartmann et al. ............ 607/1 |
| 6,915,005 | B1 | 7/2005 | Ruchala et al. |
| 7,046,831 | B2 | 5/2006 | Ruchala et al. |
| 7,186,986 | B2 | 3/2007 | Hinderer et al. |
| 7,207,715 | B2 | 4/2007 | Yue |
| 7,302,038 | B2 | 11/2007 | Mackie |
| 2002/0136439 | A1 | 9/2002 | Ruchala et al. |
| 2003/0160189 | A1 | 8/2003 | Matsuda |
| 2003/0198319 | A1 | 10/2003 | Toth et al. |
| 2005/0123092 | A1 | 6/2005 | Mistretta et al. |
| 2005/0197564 | A1 | 9/2005 | Dempsy |
| 2006/0226372 | A1 | 10/2006 | Yanagisawa |
| 2006/0285639 | A1 | 12/2006 | Olivera et al. |
| 2007/0029510 | A1 | 2/2007 | Hermann |
| 2007/0036267 | A1 | 2/2007 | Becker et al. |
| 2007/0041494 | A1 | 2/2007 | Ruchala et al. |
| 2007/0041495 | A1 | 2/2007 | Olivera et al. |
| 2007/0041496 | A1 | 2/2007 | Olivera et al. |
| 2007/0041497 | A1 | 2/2007 | Schnarr et al. |
| 2007/0041498 | A1 | 2/2007 | Olivera et al. |
| 2007/0041499 | A1 | 2/2007 | Lu et al. |
| 2007/0041500 | A1 | 2/2007 | Olivera et al. |
| 2007/0043286 | A1 | 2/2007 | Lu et al. |
| 2007/0076846 | A1 | 4/2007 | Ruchala et al. |
| 2007/0104316 | A1 | 5/2007 | Ruchala et al. |
| 2007/0195922 | A1 | 8/2007 | Mackie et al. |
| 2007/0195929 | A1 | 8/2007 | Ruchala et al. |
| 2007/0195930 | A1 | 8/2007 | Kapotoes et al. |
| 2007/0242801 | A1 | 10/2007 | Mackie et al. |
| 2008/0217561 | A1 * | 9/2008 | Mackie et al. ............ 250/492.3 |
| 2009/0289192 | A1 * | 11/2009 | Westerly et al. ......... 250/396 R |
| 2010/0006778 | A1 * | 1/2010 | Flynn et al. ............... 250/492.3 |

FOREIGN PATENT DOCUMENTS

| | | |
|---|---|---|
| EP | 0986070 A | 3/2000 |
| EP | 1045399 A | 10/2000 |
| JP | 2000 214298 A | 8/2000 |
| WO | WO02/07817 A | 1/2002 |
| WO | WO02/41948 A | 5/2002 |
| WO | WO2005/004168 A | 1/2005 |
| WO | WO2007/021226 A | 2/2007 |

OTHER PUBLICATIONS

International Search Report, PCT Application No. PCT/US2008/055070, dated Jul. 17, 2008, ISA/EPO, 2280 HV Rijswijk, NL.

International Search Report, PCT Application No. PCT/US2008/055069, dated Jul. 17, 2008, ISA/EPO, 2280 HV Rijswijk, NL.

International Search Report, PCT Application No. PCT/US2008/055161, dated Jul. 17, 2008, ISA/EPO, 2280 HV Rijswijk, NL.

International Search Report, PCT Application No. PCT/US2008/055083, dated Jul. 17, 2008, ISA/EPO, 2280 HV Rijswijk, NL.

International Search Report, PCT Application No. PCT/US2008/055096 dated Jul. 17, 2008, ISA/EPO, 2280 HV Rijswijk, NL.

International Search Report, PCT Application No. PCT/US2008/055090 dated Jul. 17, 2008, ISA/EPO, 2280 HV Rijswijk, NL.

International Search Report, PCT Application No. PCT/US2008/055147, dated Jul. 25, 2008, ISA/EPO, 2280 HV Rijswijk, NL.

Baumert, BG, et al., Dose conformation of intensity-modulated stereotactic photon beams, proton beams, and intensity-modulated proton beams for intracranial lesions, Int. J. Radiat. Oncol. Biol. Phys., 2005, 60:1314-1324, Elsevier, Amsterdam, Netherlands.

Deasy, Jo, et al., Distal edge tracking: a proposed delivery method for conformal proton therapy using intensity modulation, 1997, pp. 406-409, Proceedings of the XIIth International Congress on Computers in Radiotherapy May 27-30, 1997, Salt Lake City, IEEE Publishing, Los Alamitos, California, USA.

Deasy, Jo, A proton dose calculation algorithm for conformal therapy simulations based on Moliere theory of lateral deflections, Med. Phys., Apr. 1998, 25:476-483, American Association of Physical Medicine, New York, New York.

Lomax, AJ, Intensity modulation methods for proton radiotherapy, Phys. Med. Biol., 1999 44:185-205, IOP Publishing Ltd., Bristol, UK.

Lomax, AJ, et al. Intensity modulated proton therapy: A clinical example, Mar. 2001, Med. Phys. 28:317-324, American Association of Physical Medicine, New York, New York.

Lomax, AJ, Compensated and intensity-modulated proton therapy, in Palta J, and Mackie TR (eds), Intensity Modulated Radiation Therapy: The State of the Art, Nov. 2004, pp. 787-828, Medical Physics Publishing Madison, WI.

Lomax, AJ, et al., Treatment planning and verification of protom therapy using spot scanning: initial experiences. 2004a, Med. Phys. 31:3150-3157, American Association of Physical Medicine, New York, New York.

Lomax, AJ, et al., The clinical potential of intensity modulated proton therapy, 2004b, Z. Med. Phys. 14:147-152, Elsevier, Amsterdam, Netherlands.

Kanai, T, et al., Spot scanning system for proton radiotherapy, Jul./Aug. 1980, Med. Phys 7:365-369, American Association of Physical Medicine, New York, New York.

Moyers MF, (Proton therapy, Van Dyk (ed), The Modern Technology of Radiation Oncology, 1999, pp. 823-869, Medical Physics Publishing, Madison, WI.

Nill, S, et al., Inverse planning of intensity modulated proton therapy, 2004, Z Med. Phys. 14:35-40, Elsevier, Amsterdam, Netherlands.

Oelfke U, et al., Intensity modulated radiotherapy with charged particle beams: Studies of inverse treatment planning for rotation therapy. Jun. 2000, Med. Phys, 27:1246-1257, American Association of Physical Medicine, New York, New York.

Paganetti H, Proton Therapy: A Workshop Handout. 2005, Private Communication, Massachusetts General Hospital, Boston, MA.

Sampayan S, et al. Development of a compact radiography accelerator using dielectric wall accelerator technology, Jun. 6, 2005, Proceed. Int. Pulsed Power Conf. Monterey, CA, Lawrence Livermore Laboratory, Livermore, CA.

Wilson RW., Radiological use of fast protons. Nov. 1946, Radiology 47:487-491, Radiological Society of North America, Easton, Pennsylvania.

Yu C., Intensity modulated arc therapy with dynamic multileaf collimation: an alternative to tomotherapy, 1995, Phys. Med. Biol. 40:1435-1449, IOP Publishing Ltd., Bristol, UK.

Anferov V., Combined X-Y scanning magnet for conformal proton radiation therapy, Med. Phys. , Mar. 2005, 32:815-818, American Association of Physical Medicine, New York, New York.

Goitlein, M., Beam scanning for heavy charged particle radiotherapy, Nov./Dec. 1983, Med. Phys. 10 (6) pp. 831-840, American Association of Physical Medicine, New York, New York.

* cited by examiner

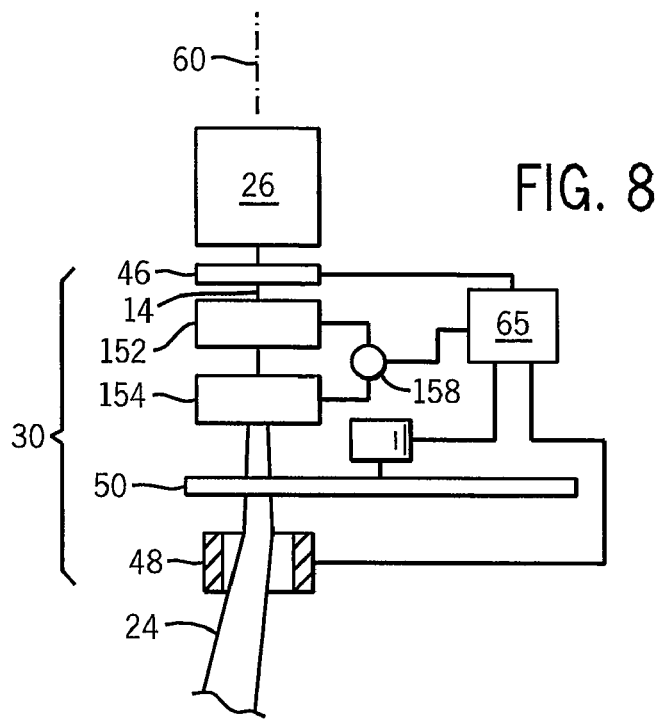
FIG. 8
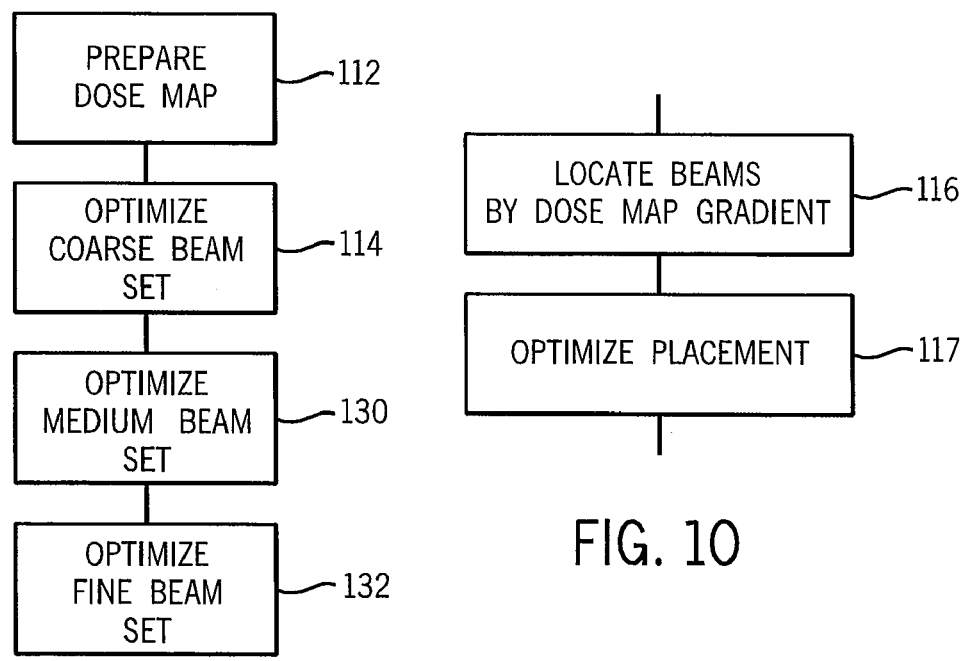
FIG. 9
FIG. 10

ION RADIATION THERAPY SYSTEM WITH VARIABLE BEAM RESOLUTION

CROSS-REFERENCE TO RELATED APPLICATIONS

This application claims the benefit of U.S. Provisional Application 60/891,859, filed Feb. 27, 2007, and PCT Application PCT/US2008/055096, filed Feb. 27, 2008, the disclosures of which are incorporated herein by reference.

STATEMENT REGARDING FEDERALLY SPONSORED RESEARCH OR DEVELOPMENT

This invention was made with United States government support awarded by the following agency: NIH CA088960. The United States government has certain rights in this invention.

BACKGROUND OF THE INVENTION

The present invention relates to radiotherapy systems using ions (such as protons) for the treatment of cancer and the like and, in particular, to a system providing improved treatment speed and accuracy.

External beam radiation therapy may treat a tumor within the patient by directing high-energy radiation in one or more beams toward the tumor. Recent advanced external beam radiation systems, for example, as manufactured by Tomotherapy, Inc., treat a tumor with multiple x-ray fan beams directed at the patient over an angular range of 360°. Each of the beams is comprised of individually modulated beamlets whose intensities can be controlled so that the combined effect of the beamlets, over the range of angles, allows an arbitrarily complex treatment area to be defined.

X-rays deposit energy in tissue along the entire path between the x-ray source and the exit point in the patient. While judicious selection of the angles and intensities of the x-ray beamlets can minimize radiation applied to healthy tissue outside of the tumor, inevitability of irradiating healthy tissue along the path to the tumor has suggested the use of ions such as protons as a substitute for x-ray radiation. Unlike x-rays, protons may be controlled to stop within the tissue, reducing or eliminating exit dose through healthy tissue on the far side of the tumor. Further, the dose deposited by a proton beam is not uniform along the entrance path of the beam, but rises substantially to a "Bragg peak" near a point where the proton beam stops within the tissue. The placement of Bragg peaks inside the tumor allows for improved sparing of normal tissue for proton treatments relative to x-ray treatments.

Current proton therapy systems adopt one of two general approaches. In the first approach, the proton beam is expanded to subtend the entire tumor and the energy of the protons, and hence their stopping point in the tissue, is spread in range, to roughly match the tumor depth. Precise shaping of the exposure volume is provided by a specially constructed range correction compensator which provides additional range shifting to conform the distal edge of the beam to the distal edge of the tumor. This treatment approach essentially treats the entire tumor at once and, thus, is fast and yet less precise and requires the construction of a special compensator.

In a second approach, the proton beam remains narrowly collimated in a "pencil beam" and is steered in angle and adjusted in range to deposit the dose as a small spot within the patient. The spot is moved through the tumor in successive exposures until an arbitrary tumor volume has been irradiated. This approach is potentially very accurate, but because the tumor is treated in successive exposures, is slower than the first approach. Further the small spot sizes create the risk of uneven dose placement or "cold spots" should there be patient movement between exposures.

SUMMARY OF THE INVENTION

The present invention provides a radiotherapy system usable with ion beams that uses multiple beam spot sizes to effect a precise trade-off between treatment speed and accuracy. For example, spatially larger beams may be used to treat large relatively homogenous portions of the treatment area with smaller beams providing precise delineation of edges and small dose features.

Specifically, the present invention provides an ion therapy machine that includes an ion source for producing an ion beam. The machine further provides a means for varying the lateral width of the ion beam (perpendicular to the propagation axis of the ion beam) as a function of a control signal and a means for steering the ion beam to different portions of a patient according to a control signal. A beam controller following a stored radiation plan communicates control signals to the means for varying the lateral width and the means for steering the ion beam to apply ion beams of different widths to different portions of the patient according to the treatment plan.

Thus, it is an object of one embodiment of the invention to aggregate treatment areas that may receive similar irradiation through the use of variable sized treatment beam, thus improving treatment speed or uniformity.

It is another object of one embodiment of the invention to allow precise tailoring of the beam spot sizes to different portions of the treatment volume to allow a flexible trade-off between treatment speed and treatment accuracy.

It is yet another object of one embodiment of the invention to provide a method of desensitizing the treatment to patient movement such as may create cold spots. The larger treatment beams naturally eliminate cold spots within the treatment beam and so it may not be necessary to employ longer treatment times to provide superior averaging of patient motion.

The invention may further include a means for varying an extent of the beams along their axis of travel (axial extent) when the beams are steered to different portions of the patient according to a control signal, and the beam controller may execute the stored radiation plan to communicate control signals to the means for varying an axial extent of the beam, to apply ion beams of different axial extents to different portions of the patient.

It is thus another object of one embodiment of the invention to change the axial extent of the beam to obtain similar benefits to those provided by the control of beam width.

The means for varying the lateral width of the beam (perpendicular to the beam axis) may be at least one focusing magnet set.

It is thus another object of one embodiment of the invention to allow control of beam size with reduced neutron generation as compared to scatter foils and the like.

It is another object of one embodiment of the invention to provide an efficient use of the energy of the proton beam by controlling beam width without the need to block portions of the beam.

A pair of successive quadrupole magnets may be used for focusing.

It is thus another object of one embodiment of the invention to provide a simple and reliable focusing structure for changing beam width.

The width of the ion beam may be adjusted by varying a separation of the quadrupole magnets or by varying the strength of at least one of the quadrupole magnets.

It is thus another object of one embodiment of the invention to provide a flexible beam width control allowing mechanical or electrical control methods.

Alternatively, the means for varying the lateral width of the beam may be a set of selectable different scattering foils movable into and out of the ion beam.

It is thus an object of one embodiment of the invention to provide a simple beam width control mechanism.

In one embodiment, the means for varying the lateral width of the beam may control the focusing drive signals of a dielectric wall accelerator.

It is thus another object of one embodiment of the invention to provide a system that will work with next generation ion sources.

The means for varying a lateral width may be a mechanical collimator.

It is thus an object of one embodiment of the invention to provide a system that may work with the current generation multi-leaf collimators or the like.

The means for varying the longitudinal and lateral extent of the beam may be a set of selectable mechanical scattering foils or ridge filters that may be moved into or out of the beam.

Thus it is an object of one embodiment of the invention to provide a simple method of controlling the axial extent of the beam.

The ion therapy machine may further include a radiation planning system receiving a dose plan for the patient and providing the radiation plan to the beam controller such that the radiation plan applies wider beams to portions of the patient with lower gradients in the dose plan and narrower beams to portions of the patient with higher dose gradients in the dose plan.

It is thus an object of one embodiment of the invention to provide a radiation planning technique adapted to exploit variable resolution ion beams.

Alternatively, the radiation plan may apply wider beams to portions of the patient removed from the edge of a tumor and narrower beams to portions of the patient at the edges of the tumor.

It is thus an object of one embodiment of the invention to provide a planning system that selects beam spot sizes based on relative location of the beams in the tumor.

The radiation planning system may provide a radiation plan to the beam controller to steer the beams to place Bragg peaks of the beams at distal edges of a tumor.

It is thus another object of one embodiment of the invention to provide a simple method of positioning the beams within the tumor volume.

These particular features and advantages may apply to only some embodiments falling within the claims and thus do not define the scope of the invention.

BRIEF DESCRIPTION OF THE DRAWINGS

FIG. 8 is a figure similar to that of FIG. 3 showing an alternative embodiment of the modulation assembly using quadrupole magnets for beam widening;

FIG. 9 is a flowchart of a treatment planning program that may work with the present invention to determine desirable beam resolution in the treatment of a patient;

FIG. 10 is a detail of the flowchart of FIG. 9 providing a step of locating the position of ion beams according to dose gradient;

DETAILED DESCRIPTION OF THE PREFERRED EMBODIMENT

Figure 1:
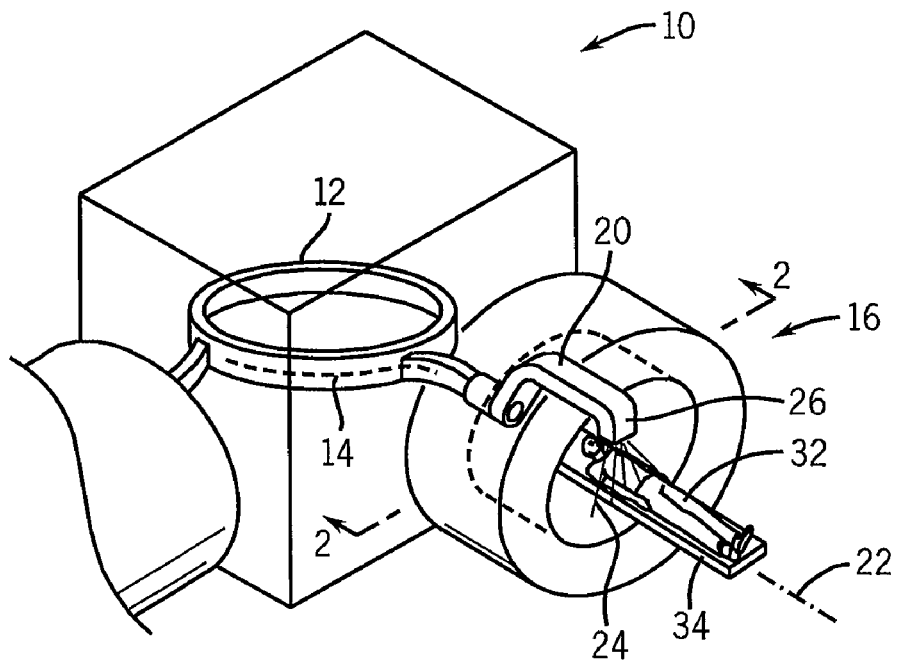
FIG. 1 is a perspective view in partial phantom of an ion therapy system suitable for use with the present invention having a synchrotron ion source providing ions to multiple gantry units.
Figure 2:
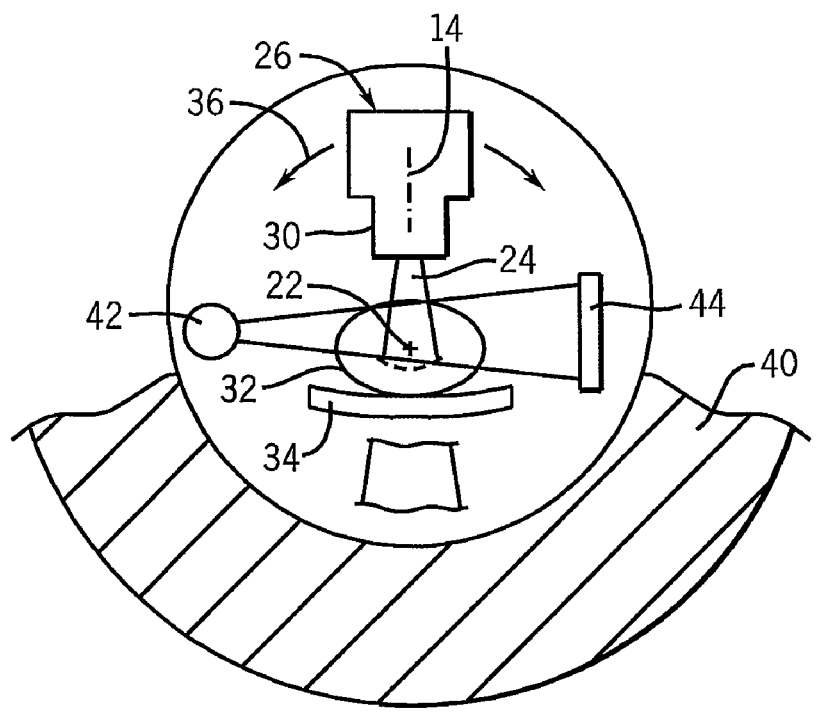
FIG. 2 is a cross-section along line 2-2 of FIG. 1 showing the path of the ion beam into a gantry to be directed into a patient after passage through a modulation assembly.

Referring now to FIGS. 1 and 2, an ion therapy system 10 may include a cyclotron or synchrotron 12 or other ion source providing a pencil beam 14 of ions that may be directed to a gantry unit 16. The pencil beam 14 may be received at the gantry unit 16 along an axis 22 into an axial portion of a rotating arm 20 rotating about the axis 22. The rotating arm 20 incorporates guiding magnet assemblies of a type known in the art to bend the pencil beam 14 radially away from the axis 22 then parallel to the axis and spaced from the axis 22 to be received by a treatment head 26. The treatment head 26 orbits about the axis 22 with rotation of the rotating arm 20 and incorporates magnets bending the ion pencil beam 14 back toward the axis 22 to intersect the axis perpendicularly.

As will be described in more detail below, the treatment head 26 may include a modulation assembly 30 to produce a variable resolution treatment beam 24. A patient 32 may be positioned on a support table 34 extending along the axis 22 so that the variable resolution treatment beam 24 may irradiate the patient 32 at a variety of angles 36 about the axis 22. A cylindrical neutron shield 40 having a bore for receiving the table 34 and the rotating arm 20 may surround the gantry unit 16 to block generated neutrons.

In one embodiment, a second rotating arm (not shown) may rotate with or independently of the rotating arm 20 to support an x-ray source 42 and x-ray detector 44 opposed across the axis 22 to illuminate the patient 32 at a range of angles to provide CT imaging capabilities according techniques well-known in the art.

Figure 3:
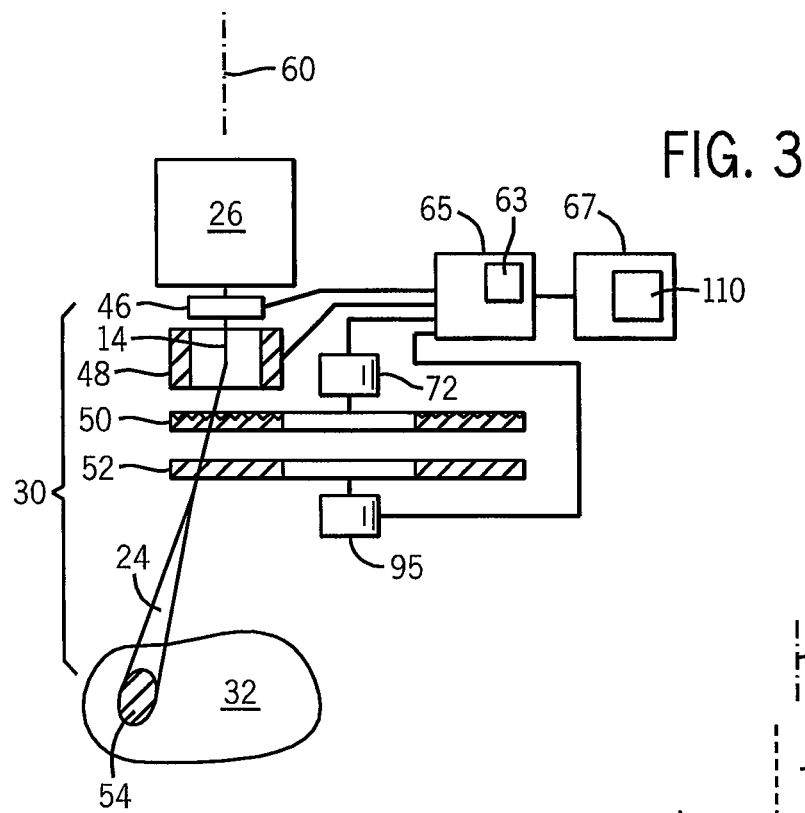
FIG. 3 is a block diagram of a first embodiment of the modulation assembly of FIG. 2.

Referring now to FIG. 3, the modulation assembly 30 produces the variable resolution treatment beam 24 by controlling the size, energy, and angle of the variable resolution treatment beam 24 to steer a variably sized treatment spot 54 through different locations within the patient 32. Specifically, the modulation assembly 30 includes a global range shifter 46 controlling the average energy of the ions in the pencil beam 14, a beam steering yoke 48 steering the pencil beam 14 in angle in one or two dimensions, a beam axial-extent controller 50 controlling a range of energies of the pencil beam 14, and a beam width controller 52 controlling a lateral width of the pencil beam in one or two dimensions. As used herein, "lateral" will refer to a direction generally perpendicular to a propagation axis of the pencil beam 14 and axial will refer to a direction generally aligned with a propagation axis of the pencil beam 14.

Each of the global range shifter 46, the beam steering yoke 48, the beam axial-extent controller 50, and the beam width controller 52, provides for electrical connections to a controller 65 that may control each of these elements electrically according to a stored a radiation plan 63. The controller 65 may communicate with a computer terminal 67 for use by a physician in preparing the radiation plan 63 according to techniques that will be described further below.

Figure 4A:
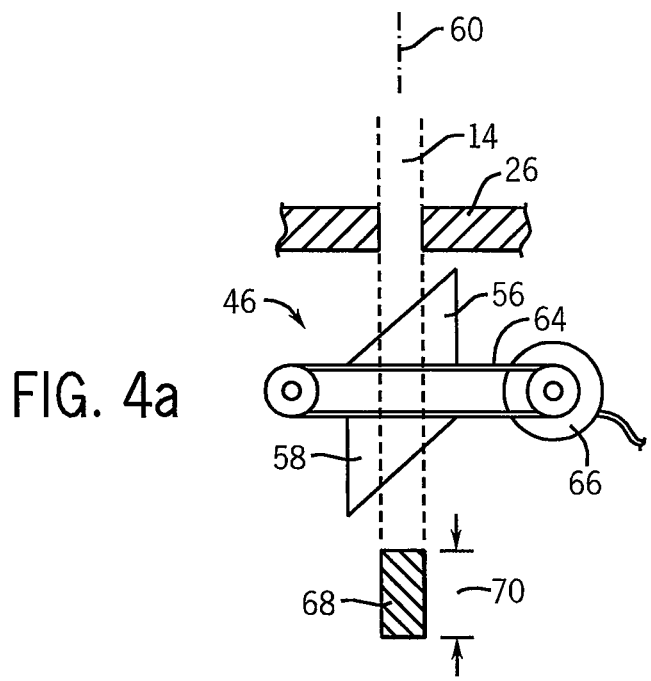
FIGS. 4a and 4b are elevational views of one embodiment of an ion range shifter assembly using counter-translating wedges, showing two positions of the wedges that provide different amounts of blocking material in the path of the ion beam to control the average ion energy.
Figure 4B:
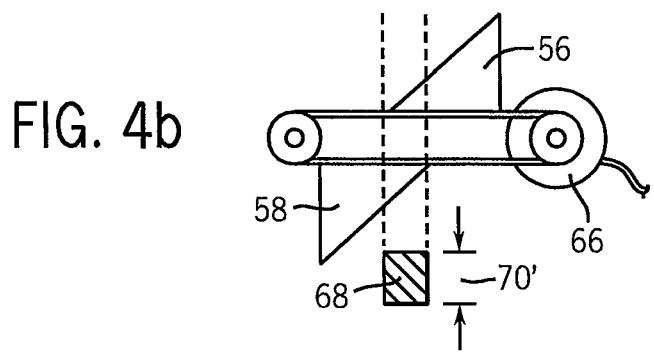

Referring now to FIG. 4, the global range shifter 46, in one embodiment, provides a first wedge 56 and second wedge 58 in the form of identical right triangles of lateral thickness (perpendicular to the plane of the triangles) equal to at least the lateral thickness of the pencil beam 14. The wedges 56 and 58 are mounted on opposite outer sides of a laterally extending belt 64 with the outer surfaces of the belt attached to corresponding bases of the wedges 56 and 58. As attached, one wedge 58 is rotated with respect to the other wedge, once about an axis aligned with the attached base and once about an axis perpendicular to the attached base.

When the belt 64 is moved by motor actuator 66 the wedges 56 and 58 move in opposite directions, with the angled hypotenuses of the wedges 56 and 58 being maintained generally parallel to each other. It will be understood that in this configuration that when the pencil beam 14 passes through both of the wedges 56 and 58 it will pass through a constant amount of wedge material over the entire lateral extent of the pencil beam 14, providing uniform energy attenuation of the photons of the pencil beam 14. In a first position of the wedges 56 and 58, shown in FIG. 4a, with the wedges 56 and 58 fully overlapping in an axial direction, the combined material of the wedges 56 and 58 forms an equivalent rectangular bolus 68 having a first height 70. In a second position of the wedges 56 and 58, shown in FIG. 4b, with the wedges 56 and 58 axially separated by a full amount still allowing them to overlap in the area of the pencil beam 14, the equivalent rectangular bolus 68 has a second height 70' less than the first height 70. The height of the equivalent bolus 68 controls the average energy of the protons in the pencil beam 14 and thus movement of the wedges 56 and 58 allows control of the depth of the treatment spot 54 within the patient. The motor actuator 66 may be, for example, a stepper or servomotor as is understood in the art.

Referring again to FIG. 3, after the pencil beam 14 has passed through the global range shifter 46, the pencil beam 14 is received by a beam steering yoke 48 which may, for example, be a set of electromagnetic coils or opposed electrostatic plates well known for steering charged particles in one or two lateral dimensions. The beam steering yoke 48 allows the pencil beam 14 to be steered at an angle from an axis 60 perpendicular to the axis 22 about which the beam rotates. In this way the treatment spot 54 to be moved to an arbitrary lateral location within the patient 32. Together these beam steering yokes 48 and the range shifter 46 allow the treatment spot 54 to be moved to arbitrary locations within the patient 32.

Figure 5:
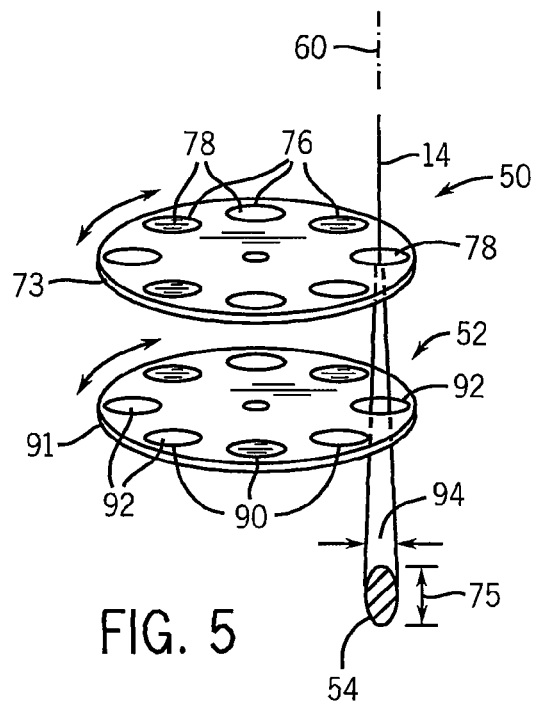
FIG. 5 is a perspective view of two rotating disks holding different scattering foils and ridge filters respectively, to control beam width and beam axial extent.

Referring now to FIGS. 3 and 5, the size of the treatment spot 54, in terms of axial length, is controlled by the beam axial-extent controller 50 which varies the energies of the ions in the pencil beam 14 to create one of a number of predefined energy ranges. In one embodiment, the beam axial-extent controller 50 uses a disk 73 extending in a lateral plane and rotatable by motor 72 about an axis parallel to the axis of the pencil beam 14, to bring various apertures 76 in the periphery of the disk into alignment with the pencil beam 14 as the disk is rotated. Each of the apertures 76 may be fitted with a different ridge filter 78 providing for a different spread of energies and thus a different axial length 75 of the treatment spot 54.

Figure 6:
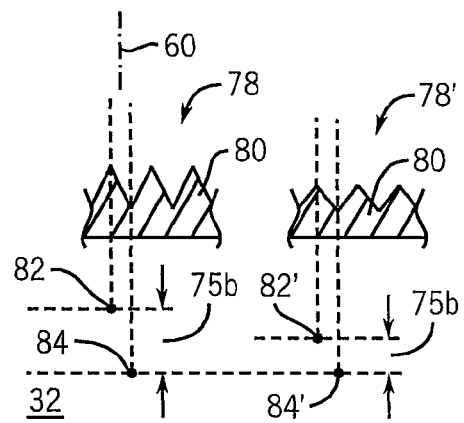
FIG. 6 is an elevational cross-section of two ridge filters of the disk of FIG. 5 such as provide different axial extents of an ion beam.

Referring to FIG. 6, a first axial ridge filter 78, for example in a first aperture 76, may have a set of triangular ridges 80 whose peaks provide a first axial thickness to reduce ions' energies to provide an average stopping point 82 in the patient 32, and troughs having reduced thickness and allowing increased proton energy to provide an average stopping point 84 in the patient 32. The difference between these two stopping points 82 and 84 represents the axial length 75a of the treatment spot 54.

For comparison, a second ridge filter 78' in a different aperture 76, may have a similar profile but with ridges of lesser amplitude whose peaks provide a first stopping point 82' and whose troughs provide a second stopping point 84' that are closer together to produce an axial length 75b that is substantially shorter than the axial length 75a. A number of different filters 78 may provide for a range of different axial lengths 75 for the treatment spot 54.

Referring still to FIGS. 3 and 5, the beam width controller 52 may be a similar disk 91 positioned below disk 73 and axially aligned therewith and rotatable by motor 95 to bring various apertures 90 in the periphery of the disk 91 into alignment with the pencil beam 14. In this case, the apertures 90 may be fitted with different scattering foils 92 such as cause a lateral spreading of the pencil beam 14 by various amounts according to the material and thickness of the scattering foil to control the lateral width 94 of the treatment spot 54.

Figure 7:
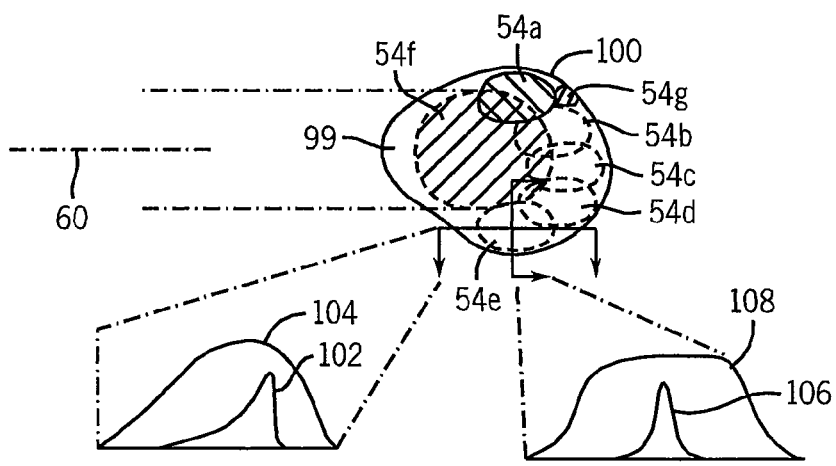
FIG. 7 is a schematic representation of a dose map for a patient, the dose map having treatment zones and showing different width beams superimposed on the dose map, and further showing the axial and lateral profiles of those beams.

Referring now to FIG. 7, a radiation plan 63 describing the positioning of the multiple treatment spots 54 and their sizes may be developed with reference to a dose map 100 prepared by a physician using planning software to convert the dose map 100 to a radiation plan 63. The dose map 100 may be prepared, for example, using a graphics terminal with the physician viewing one or more CT images of the patient to define desired doses in different zones within the volume of the patient.

A simple dose map 100 follows the outline of a tumor 99 and provides a desired uniform dose within that outline. The present invention may provide a radiation plan 63 that uses multiple treatment spots 54a-54f to deliver the desired dose. Generally the axial length of the treatment spot 54 will affect the profile of the dose within the treatment spot 54. Thus, for example, a small treatment spot 54e will have an axial profile 102 exhibiting a well-defined Bragg peak with a sharp distal fall off whereas a large treatment spot 54f will exhibit an axial profile 104 with a more gradual falloff being the aggregate of Bragg peaks for multiple protons of different energies. For this reason, smaller treatment spots 54 may preferentially be used near the distal edge of the tumor or at other points of high dose gradient.

The lateral width of the treatment spot 54 will also affect the lateral profile of the dose within the treatment spot 54. In this case the lateral falloff is not determined by the Bragg peak but simply by beam spreading after collimation.

Intuitively, it will be understood from FIG. 7 that a large treatment spot 54*f* may be advantageously placed roughly centered within the tumor 99 and smaller treatment spots 54*a*-54*e* may be used close to the distal edge of the tumor 99 to take advantage of the sharper Bragg peak available from those smaller spots. As the gantry is rotated and axis 60 of the pencil beam 14 moves about the tumor 99, different edges of the tumor 99 become the distal edge allowing this approach to be repeated for the entire tumor 99 to provide sharp demarcation of the outline of the tumor 99.

This general observation may be exploited more precisely by a radiation treatment planning system implemented by program 110 executed in the terminal 67 to prepare a radiation plan 63. Referring now to FIGS. 7 and 9, the treatment plan may begin by receiving a dose map 100 as indicated by process block 112 generally describing a spatial extent of a portion of the patient 32 where an ion dose will be applied. In contrast to the dose map 100 of FIG. 7, the dose map 100 more generally will include multiple zones within a dose map 100 describing variations in the intensity of the doses within those zones.

At process block 114, a first set of beams, for example, producing large treatment spots 54*f* may be fit to the dose map 100. This fitting determines both an intensity of the different treatment spots 54 and the location of the beam treatment spot 54. One method for locating the treatment spot 54 tries to fit as many of the treatment spots 54 into the tumor area of the dose map 100 as can be done with controlled overlapping or extending outside of the tumor 99. The intensities may then be determined by an iterative process, for example "simulated annealing", considering multiple exposures for different gantry angles.

Once the intensity of the large treatment spot 54 is determined, then at process block 130 smaller treatment spots 54 (for example treatment spot 54*a*-*e*) are positioned on the dose map 100 in gaps between the larger treatment spots 54*f*. These gaps may be identified simply by creating a difference map indicating differences between the dose implemented by the large treatment spots 54*f* and the desired dose of the dose map 100, and placing the smaller treatment spots 54*a*-*e* according to the difference map. The intensities and positions of the optimized larger treatment spots 54*f* are held fixed and only the intensities of the new smaller treatment spots 54*a*-*e* are optimized iteratively. Alternatively, the intensities and positions of the optimized larger treatment spots 54*f* may be used as a starting position for renewed optimization of both the larger treatment spots 54*f* and the new smaller treatment spots 54*a*-*e*.

As illustrated by process block 132, this process may be repeated for yet smaller treatment spots 54*g* shown in FIG. 7.

Figure 11:
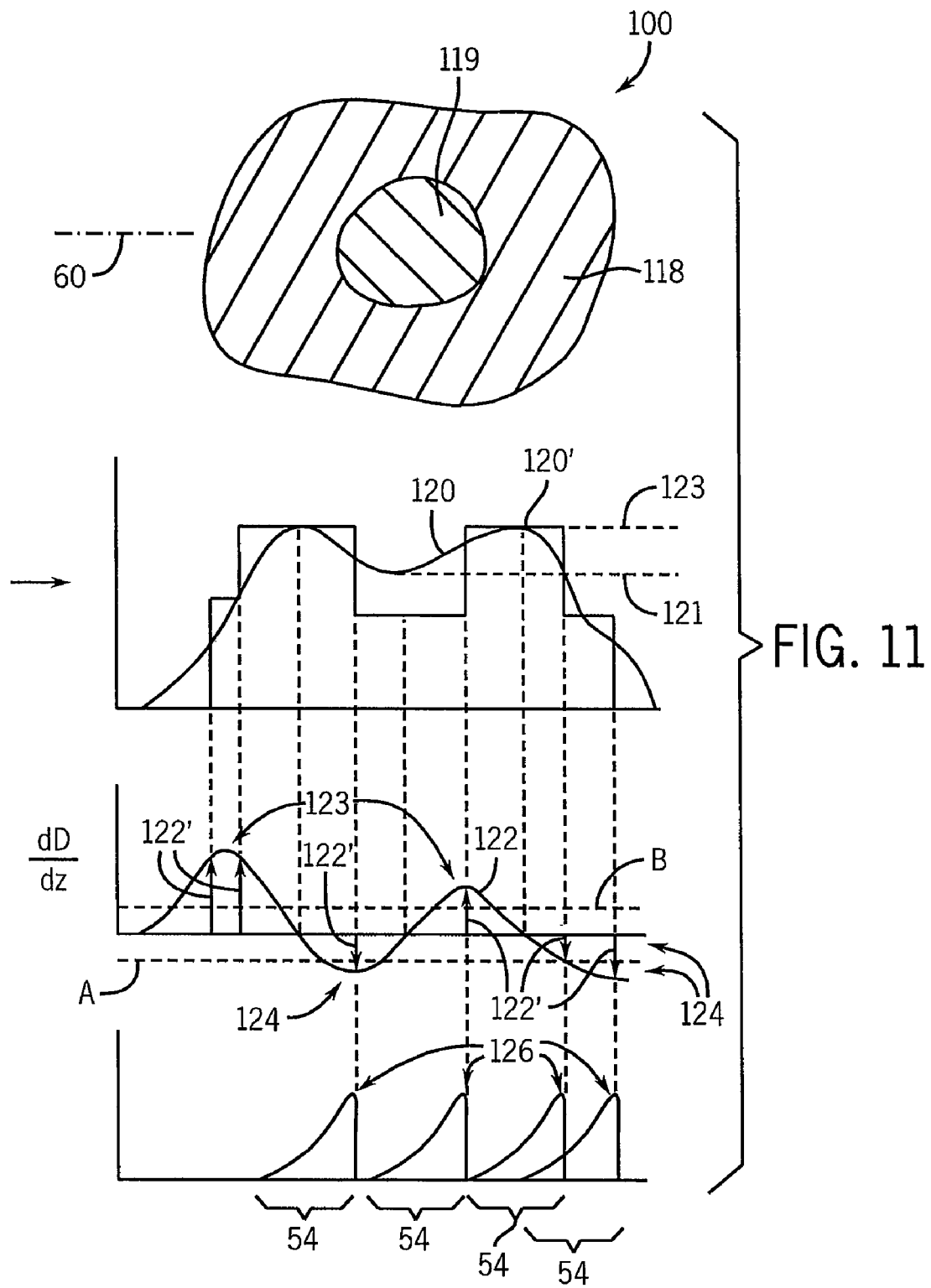
FIG. 11 is a representation of a non-uniform dose map, its gradient along one axis, and a positioning of a Bragg peak of ion beams of different resolutions based on those gradients.

Referring now to FIGS. 10 and 11, an alternative method of locating the treatment spots 54, as indicated by process block 116, determines a gradient 122 of the dose map 100 being the spatial derivative of the dose 120 along a particular treatment axis (e.g. aligned with axis 60 for each treatment fraction). For simplicity, the dose map 120 may be discretized into two or more dose levels as shown by discretized dose map 120' and a discretized gradient 122' developed (indicating generally gradient sign).

For example, the dose map 100 may include a first central zone 119 of lower dose 121 and an outer peripheral zone 118 of higher dose 123. Discretized derivative values 122' along axis 60 may provide for two positive going transitions 123, a negative going transitions 124, a positive going transition 123, and two negative going transitions 124 (from left to right) following the discretized gradient 122'. These transitions 123 and 124 may be used to align the Bragg peak 126 of treatment spots 54 to provide a location of those beam spots for intensity optimization according to the following rules:

(a) place a Bragg peak 126 along the ray of a given proton beam at points where the dose gradient drops below a user-defined negative threshold (A) (or in the case of the discretized gradient 122', where there are negative transitions);

(b). place a Bragg peak 126 along the ray of a given proton beam at points where the dose gradient exceeds below a user-defined negative threshold (B) (or in the case of the discretized gradient 122', where there are positive transitions) after there has been at least one peak placed per (a) above.

The height of the peaks 124 may also be matched to the steepness of the Bragg peaks 124 of the different sizes of treatment spots 54 which, as noted, before, tend to vary with the treatment spot 54 size.

Once locations of treatment spot 54 are fixed, the intensities may be optimized as described before or by iterative techniques such as Simulated Annealing or Gradient Based Optimization Techniques beams at multiple angles. Multiple delivery angles, for example over 360 degrees, and control of the intensity of the beam spots will then build up the dose to match the dose map 100. By selecting a beam range prior to iteration, the iteration process is much simplified.

Alternatively or in addition, the above technique of locating the Bragg peaks of the treatment spots 54 may be used on an "ex ante" basis and an optimization program 117 may then be run in which the dose produced by the ex ante placement is compared to the desired dose. The deficiency in the dose is then used to place additional treatment spots 54. In this way locations that did not receive a sufficient amount of dose from the first pass are filled in with spots that are added based on the difference.

Referring now to FIG. 8, in an alternative embodiment of the modulation assembly 30, axial range shifter 46 may be followed by a first and second quadrupole magnet 152 and 154 rotated along axis 60 at 90 degrees with respect to each other. The pencil beam 14 passing through the successive quadrupole magnets 152 and 154 is expanded into a diverging fan beam. The width of this diverging fan beam may be controlled by changing the separation of the quadrupole magnets 152 and 154 by a mechanical focusing assembly 158, and/or by control of the strength of the magnets in one or both quadrupole magnets 152 and 154 by controlling an electromagnetic current according to signals from the controller 65.

The variable resolution treatment beam 24 from the quadrupole magnets 152 and 154 is then received by the beam axial-extent controller 50 and then steered by beam steering yoke 48 as described before.

Figure 12:
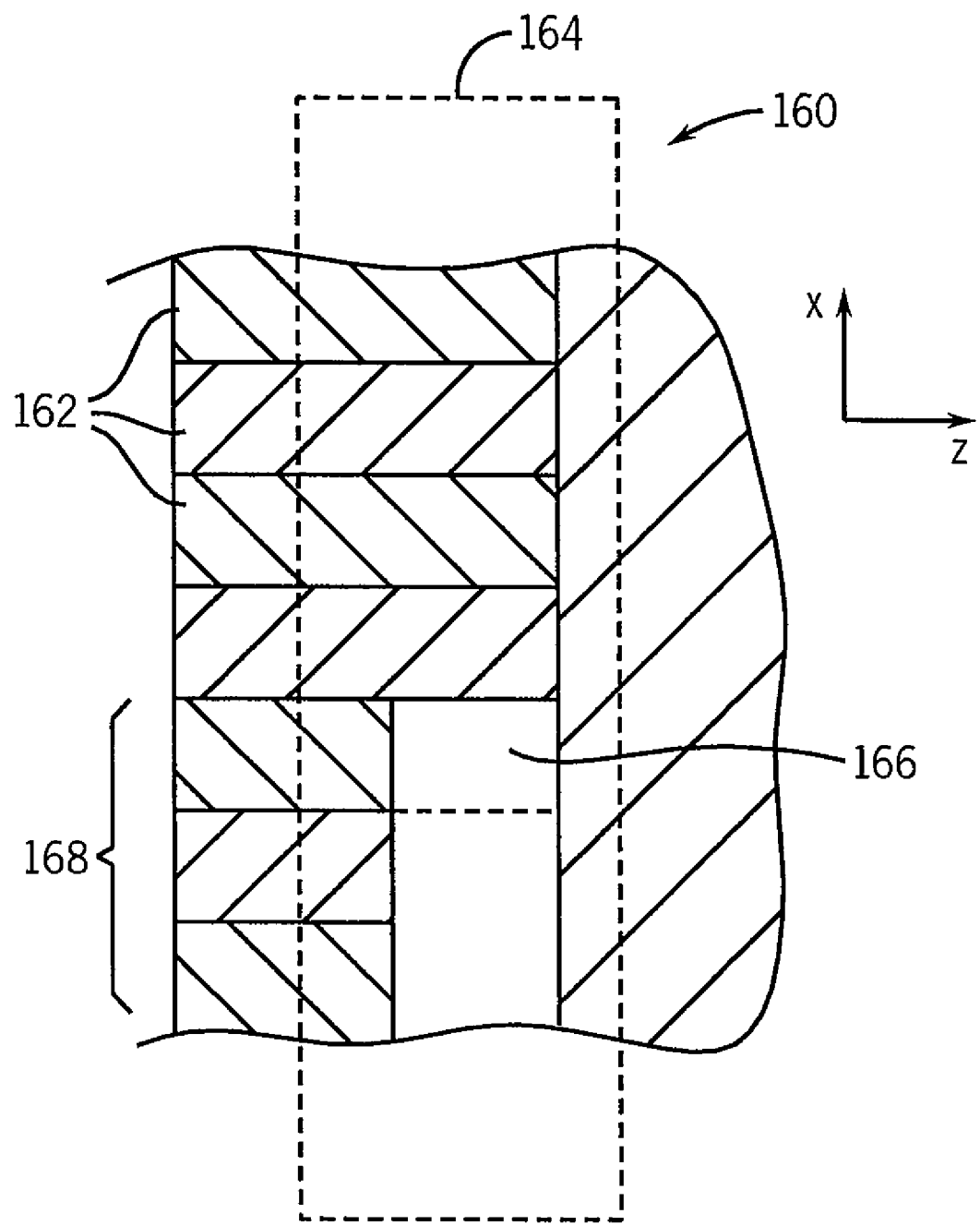
FIG. 12 is a plan view of a multi-leaf collimator that may be operated to effectively control beam widths and beam locations.

Referring now to FIG. 12, control of the beam width and its location may, in an alternate embodiment, be accomplished by a multi-leaf collimator 160 having individually controllable leaves 162 which may be moved into or out of a fan beam 164 to create apertures 166 defining beam widths 168 and, by their offset from a center of the fan beam 164, may control the positioning of the beam within the patient 32. Thus one mechanism may provide both for steering and beam width control, the separate control signals being combined to produce control signals for selection of particular shutters for opening and/or closing. A shutter system suitable for this use is described in U.S. Pat. No. 5,668,371 described above. Although only a single aperture 166 is shown, in the simplest embodiment, this technique may be used to produce simultaneous multiple apertures (not shown) of different widths for concurrent treatment using the same axial extent or variable axial extent provided by corresponding range shifters for each aperture, again as taught in U.S. Pat. No. 5,668,371.

Generally, the invention anticipates that the source of protons may also be a dielectric wall accelerator. As is understood in the art a dielectric wall accelerator provides a linear acceleration of charged particles through the use of successively applied electrostatic fields that serve to accelerate the charged particles as they move through the dielectric wall accelerator. Energy modulation may be obtained by simply controlling the degree of acceleration of the charged particle through the switching of the electrostatic fields and their timing. The beam widths may be controlled by electronic control of focusing electrodes incorporated into the body of the dielectric wall accelerator. By deflecting the protons at the proximal end of the dielectric wall accelerator early in the acceleration process, it is believed that it should be possible to steer the proton beam. The electrodes used to control the beam width can also be used for focusing the beam spot.

Dielectric wall accelerators suitable for this purpose are described for example in "Development of a Compact Radiography Accelerator Using Dielectric Wall Accelerator Technology" by Sampayan, S. et als. Proceedings of the Particle Accelerator Conference, 2005. PAC 2005. Publication Date: 16-20 May 2005 pp: 716-718 ISBN: 0-7803-8859-3.

The present invention contemplates changing of the size of the treatment spot 54 in three dimensions: axially and in two perpendicular lateral directions. The present invention may also be used with beam spot control in only two dimensions: axial and one lateral dimension within a plane of rotation of the gantry head 26. Under this control technique the patient may be treated on a slice-by-slice basis through a "rotate and step" scanning pattern or a helical scanning pattern of a type known in the art for x-ray tomography.

Alternatively such a system may also combine helical scanning, for example, with variable beam widths in three dimensions including along the axis about which the head 26 is rotated. Such a system would anticipate common structure in adjacent slices to provide for treatment of these structures over a longer period during multiple slices.

It is specifically intended that the present invention not be limited to the embodiments and illustrations contained herein, but include modified forms of those embodiments including portions of the embodiments and combinations of elements of different embodiments as come within the scope of the following claims.

We claim:

1. An ion therapy machine comprising:
an ion source for producing an ion beam traveling along an axis;
means for varying a lateral width of the ion beam perpendicular to the axis as a function of a control signal;
means for varying an axial extent of the beams when steered to portions of the patient according to a control signal;
means for steering a center of the ion beam to different portions of a patient according in both lateral and axial dimensions to a control signal; and
a beam controller executing a stored radiation plan to communicate control signals to the means for varying a lateral width, the means for varying an axial extent and the means for steering the ion beam, to provide a radiation treatment to the patient by applying ion beams of different widths to different portions of the patient.

2. The ion therapy machine of claim 1 further including:
apparatus for rotating the axis of the ion beam to different angles with respect to the patient; and
wherein the beam controller further executes the stored radiation plan to communicate control signals to the means for varying an axial extent, the means for varying the lateral width and steering means to apply ion beams with higher gradients at the distal edge of the tumor than at a center of the tumor.

3. The ion therapy machine of claim 1 wherein the means for varying a lateral width is a pair of successive quadrupole magnets and the width of the ion beam is adjusted by varying a separation of the quadrupole magnets.

4. The ion therapy machine of claim 1 wherein the means for varying an axial extent is a set of selectable mechanical ridge filters.

5. The ion therapy machine of claim 1 wherein the means for varying a lateral width is a mechanical collimator.

6. The ion therapy machine of claim 1 further including a radiation planning system receiving a dose plan for a tumor within the patient and providing the radiation plan to the beam controller such that the radiation plan applies wider beams to portions of the tumor with higher gradients of the dose plan and narrower beams to portions of the tumor with lower dose gradients of the dose plan in regions removed from edges of the tumor.

7. The ion therapy machine of claim 1 further including a radiation planning system receiving a dose plan for the patient and providing the radiation plan to the beam controller to steer the beams to place Bragg peaks of the beams at distal edges of a tumor.

8. A method of radiation treatment with an ion beam traveling along an axis comprising the steps of:
executing a stored radiation treatment plan to:
(a) vary a lateral width of the ion beam perpendicular to the axis according to beam width data in the radiation treatment plan;
(b) vary an axial extent of the ion beam along the axis according to beam extent data in the radiation treatment plan;
(c) steer the axis of the ion beam to different portions of a patient according to beam location data in the radiation treatment plan;
whereby ion beams of different widths and extents are applied to at least two different portions of the patient.

* * * * *